(12) United States Patent
Yomtov

(10) Patent No.: US 8,739,788 B2
(45) Date of Patent: Jun. 3, 2014

(54) VAPORIZER HEATING ASSEMBLY AND METHOD OF REGULATING A TEMPERATURE WITHIN THE VAPORIZER HEATING ASSEMBLY

(75) Inventor: Amir Yomtov, Boca Raton, FL (US)

(73) Assignee: Vaporfection International, Inc., Deerfield Beach, FL (US)

( * ) Notice: Subject to any disclaimer, the term of this patent is extended or adjusted under 35 U.S.C. 154(b) by 65 days.

(21) Appl. No.: 13/204,432

(22) Filed: Aug. 5, 2011

(65) Prior Publication Data
US 2012/0152244 A1   Jun. 21, 2012

Related U.S. Application Data

(60) Provisional application No. 61/424,102, filed on Jan. 7, 2011.

(51) Int. Cl.
*F28D 7/10*          (2006.01)
*A61M 11/04*       (2006.01)

(52) U.S. Cl.
CPC . *F28D 7/10* (2013.01); *A61M 11/04* (2013.01)
USPC ............. 128/204.17; 128/203.27; 128/203.26

(58) Field of Classification Search
CPC ..... A61M 11/041; A61M 11/04; F28D 7/106; F28D 7/103; F28D 7/12
USPC ............. 128/200.24, 203.12, 203.15, 203.16, 128/203.17, 203.26, 203.27, 204.17, 128/204.18, 204.21
See application file for complete search history.

(56) References Cited

U.S. PATENT DOCUMENTS

| | | | | |
|---|---|---|---|---|
| 3,951,175 A | * | 4/1976 | Eberhart | 138/178 |
| 3,968,346 A | * | 7/1976 | Cooksley | 392/491 |
| 4,511,435 A | * | 4/1985 | Strohschein | 202/158 |
| 4,729,365 A | | 3/1988 | Mutchler | |

(Continued)

FOREIGN PATENT DOCUMENTS

JP          62-000763 A       1/1987
JP          09-294805 A      11/1997

*Primary Examiner* — Annette Dixon
(74) *Attorney, Agent, or Firm* — The Concept Law Group, P.A.; Scott D. Smiley; Yongae Jun

(57) ABSTRACT

A method of regulating a temperature within a vaporizer heating assembly includes providing a vaporizer heating assembly that includes a vapor inhalation device shaped to contain a vapor and deliver the vapor to a user's mouth without expelling the vapor into the atmosphere, an airflow chamber mechanically coupled to the vapor inhalation device, a heating chamber disposed within the airflow chamber, a fan in fluid communication with an air passageway defined by an interior surface of the airflow chamber and an exterior surface of the heating chamber, a temperature probe disposed proximate, but not in direct physical contact with the airflow chamber, and a temperature controller thermally coupled to the temperature probe and communicatively coupled to the heating chamber, the temperature controller operable to control a temperature output of the heating chamber in response to temperature information received from the temperature probe. The method further includes the steps of sensing a temperature of an area surrounding a portion of the airflow chamber with the temperature probe, communicating the sensed temperature of the area surrounding a portion of the airflow chamber to the temperature controller, operating the fan to direct air into a proximal end of the airflow chamber, sensing with the temperature probe a change in the temperature of the area surrounding the portion of the airflow chamber, and communicating the sensed temperature change to the temperature controller.

19 Claims, 8 Drawing Sheets

(56) References Cited

U.S. PATENT DOCUMENTS

| | | | | |
|---|---|---|---|---|
| 4,967,744 A | * | 11/1990 | Chua | 128/204.18 |
| 5,031,612 A | * | 7/1991 | Clementi | 128/204.14 |
| 5,033,541 A | * | 7/1991 | D'Silva | 165/155 |
| 5,400,602 A | * | 3/1995 | Chang et al. | 62/50.7 |
| 5,819,756 A | | 10/1998 | Mielordt | |
| 6,078,730 A | * | 6/2000 | Huddart et al. | 392/480 |
| 6,095,139 A | * | 8/2000 | Psaros | 128/204.22 |
| 6,167,883 B1 | * | 1/2001 | Beran et al. | 128/203.17 |
| 6,662,802 B2 | * | 12/2003 | Smith et al. | 128/203.16 |
| 6,761,164 B2 | | 7/2004 | Amirpour et al. | |
| 6,772,756 B2 | | 8/2004 | Shayan | |
| D549,313 S | | 8/2007 | Kelnhofer | |
| 7,445,007 B2 | | 11/2008 | Balch et al. | |
| 7,475,684 B2 | | 1/2009 | Balch et al. | |
| 7,624,734 B2 | | 12/2009 | Balch et al. | |
| 2006/0283447 A1 | * | 12/2006 | Dhuper et al. | 128/203.12 |
| 2008/0173300 A1 | * | 7/2008 | Justman | 128/200.11 |
| 2011/0108031 A1 | * | 5/2011 | Korneff et al. | 128/203.27 |
| 2012/0152244 A1 | * | 6/2012 | Yomtov | 128/203.14 |
| 2012/0152246 A1 | * | 6/2012 | Yomtov | 128/203.26 |

* cited by examiner

VAPORIZER HEATING ASSEMBLY AND METHOD OF REGULATING A TEMPERATURE WITHIN THE VAPORIZER HEATING ASSEMBLY

FIELD OF THE INVENTION

The present invention relates generally to a vaporizer for inhalation of active ingredients within a plant material, and more particularly relates to a heating assembly within a vaporizer that provides improved airflow, longer life, reduced taste emissions, and superior temperature control.

BACKGROUND OF THE INVENTION

A vaporizer is a device used to extract the active ingredients of plant material, e.g., cannabis, tobacco, or other herbs or blends, for inhalation by a human. Vaporization involves heating a material so that its active compounds boil off into a vapor. As opposed to smoking, i.e., burning, vaporization avoids the production of irritating, toxic, and carcinogenic by-products. In fact, no combustion occurs, so no smoke or taste of smoke is present. Studies show that vapor contains substantially zero particulate matter or tar, and, in comparison to smoking, significantly lower concentrations of noxious gases such as carbon monoxide. It has also been shown that, in comparison to other drug delivery methods, such as ingestion, vaporization has a more rapid onset of pharmacological effect, direct delivery into the bloodstream (via the lungs), and more precise titration such that the desired level is reached and not exceeded, enabling consistent and appropriate dosage.

Prior-art vaporizers use a heating element that adds an unpleasant taste to the air stream flowing through it. In addition, all known vaporizers are made with a heating element inside an air-flow conduit where the heating element rests against a portion of the interior of the conduit, thereby preventing air from flowing around certain portions of the heating element, resulting in non-optimized airflow and/or heat exchange. Furthermore, prior-art vaporizers utilize temperature probes that are installed within the air-flow conduit. These probes are in direct thermal communication with the airflow and are heavily influenced by changes in the temperature of the air flowing by the heating element. The temperature controllers attached to the probes respond to this temperature change, often unnecessarily and too severely, thereby resulting in a sinusoidal pattern in the heating taking place within the heating element, resulting in too high or too low of temperatures and adverse effects to the user's experience.

Therefore, a need exists to overcome the problems with the prior art as discussed above.

SUMMARY OF THE INVENTION

The invention provides a vaporizer heating assembly that overcomes the hereinafore-mentioned disadvantages of the heretofore-known devices and methods of this general type and that maximizes efficiency of heat transfer between a heating element and a passing stream of air. The invention also provides proved consistency of heating-element temperature monitoring and control.

With the foregoing and other objects in view, there is provided, in accordance with the invention, a vaporizer heating assembly includes a vapor inhalation device shaped to contain a vapor and deliver the vapor to a user's mouth without expelling the vapor into the atmosphere, an airflow chamber mechanically coupled to the vapor inhalation device, a heating chamber disposed within the airflow chamber, a fan in fluid communication with an air passageway defined by an interior surface of the airflow chamber and an exterior surface of the heating chamber, a temperature probe disposed proximate, but not in direct physical contact with the airflow chamber, and a temperature controller thermally coupled to the temperature probe and communicatively coupled to the heating chamber, the temperature controller operable to control a temperature output of the heating chamber in response to temperature information received from the temperature probe.

In accordance with a further feature of the present invention, the airflow chamber includes a proximal end, a distal end coupled to the vapor inhalation device, and a glass body connecting the proximal end to the distal end.

In accordance with another feature of the present invention, the glass heating chamber includes an elongated glass body and a heating element disposed within the elongated glass body of the heating chamber.

In accordance with one more feature of the present invention, the airflow chamber defines a longitudinal central axis and a longitudinal central axis of the heating chamber is substantially collinear with the longitudinal central axis of the airflow chamber.

In accordance with yet another feature of the present invention, a location of the heating chamber within the airflow chamber provides an airflow path between the heating chamber and an interior surface of the airflow chamber on all sides of the heating chamber.

In accordance with an additional feature of the present invention, the airflow chamber further includes a plurality of interiorly-pointing features along an interior wall of the glass body of the airflow chamber, wherein the heating chamber is physically supported by the plurality of interiorly-pointing features.

In accordance with another feature, an embodiment of the present invention also includes a filter at the distal end of the airflow chamber.

In accordance with yet another feature, an embodiment of the present invention includes a method of regulating a temperature within a vaporizer heating assembly, where the method include the step of providing a vaporizer heating assembly that features a vapor inhalation device shaped to contain a vapor and deliver the vapor to a user's mouth without expelling the vapor into the atmosphere, an airflow chamber mechanically coupled to the vapor inhalation device, a heating chamber disposed within the airflow chamber, a fan in fluid communication with an air passageway defined by an interior surface of the airflow chamber and an exterior surface of the heating chamber, a temperature probe disposed proximate, but not in direct physical contact with the airflow chamber, and a temperature controller thermally coupled to the temperature probe and communicatively coupled to the heating chamber, the temperature controller operable to control a temperature output of the heating chamber in response to temperature information received from the temperature probe. The method further includes the steps of sensing a temperature of an area surrounding a portion of the airflow chamber with the temperature probe, communicating the sensed temperature of the area surrounding a portion of the airflow chamber to the temperature controller, operating the fan to direct air into a proximal end of the airflow chamber, sensing with the temperature probe a change in the temperature of the area surrounding the portion of the airflow chamber, and communicating the sensed temperature change to the temperature controller.

In accordance with yet another feature, an embodiment of the present invention includes a heating assembly with a tubular airflow chamber that defines a proximal end, a distal end opposite the proximal end, and a glass body connecting the proximal end to the distal end, the glass body having a plurality of indentions extending into an interior defined by the glass body. A heating chamber is disposed within the airflow chamber and supported along a central axis of the airflow chamber by the plurality of indentions, where the heating chamber has an elongated glass body and a heating element disposed within the elongated glass body of the heating chamber. A fan is in fluid communication with the airflow chamber and positioned relative to the airflow chamber so that, when operated to blow air, causes air to flow into the proximal end of the airflow chamber, across all sides of the heating element, and out of the distal end of the airflow chamber.

In accordance with a further feature of the present invention, a vaporizer assembly includes a heating assembly with a glass airflow chamber and a glass heating chamber disposed substantially along a central axis within the glass airflow chamber. A fan is in fluid communication with the heating assembly and is positioned relative to the airflow chamber so that, when operated, causes air to flow into a proximal end of the airflow chamber, across all sides of the heating element, and out of a distal end of the airflow chamber. An attachment adapter mechanically coupled to the distal end of the airflow chamber is in a sealing arrangement, where the attachment adapter forms an attachment port for a vapor receiving element.

Although the invention is illustrated and described herein as embodied in a vaporizer heating assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the heating element assembly.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
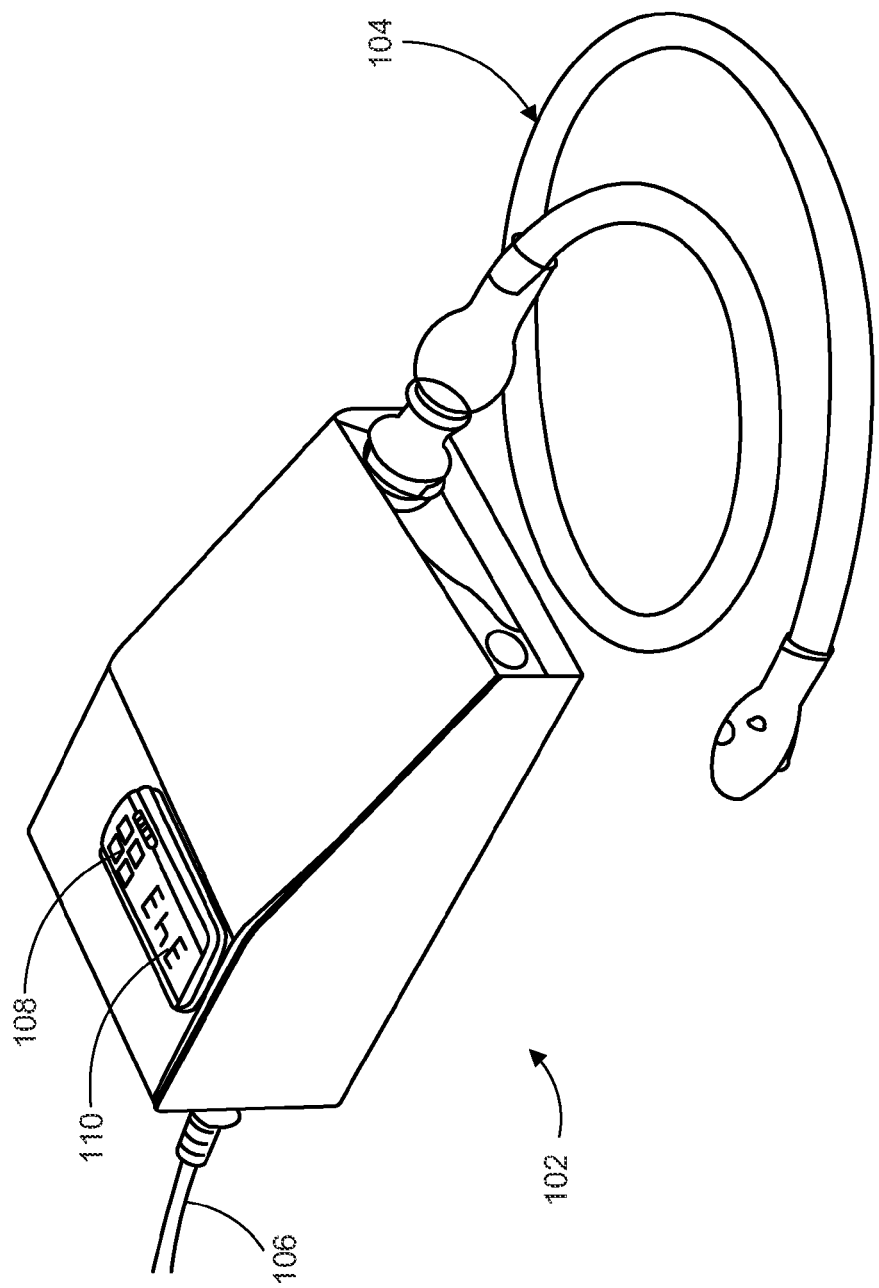
FIG. 1 is a perspective view of a control box and whip in accordance with an exemplary embodiment of the present invention.

While the specification concludes with claims defining the features of the invention that are regarded as novel, it is believed that the invention will be better understood from a consideration of the following description in conjunction with the drawing figures, in which like reference numerals are carried forward, it is to be understood that the disclosed embodiments are merely exemplary of the invention, which can be embodied in various forms.

The present invention provides a novel and efficient heating element assembly and accurate and stable temperature control of said element. Embodiments of the invention provide a glass-on-glass heating element configuration that optimizes heat transfer to a passing flow of air. In addition, embodiments of the invention provide a temperature sensor and control circuit for monitoring the inventive heating element and providing optimized temperature stability and control.

Referring now to FIG. 1, one embodiment of the present invention is shown in a perspective view. The figures of the instant application show several advantageous features of the present invention, but, as will be described below, the invention can be provided in several shapes, sizes, combinations of features and components, and varying numbers and functions of the components. The first example of a vaporizer, as shown in FIG. 1, includes a control box 102 and a vapor inhalation device, e.g., a long flexible drawtube ("whip"), 104 through which the user inhales the vapor, reducing its temperature on arrival. The vapor inhalation device 104 provides an airtight sealed pathway between the control box 102 and the user's mouth.

Figure 2:
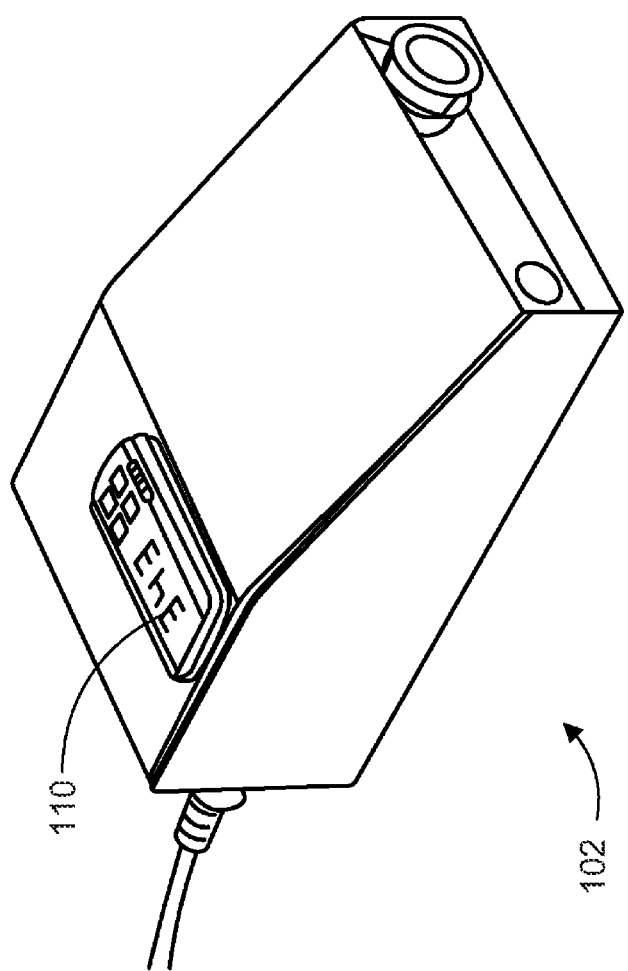
FIG. 2 is a close-up perspective top view of the control box of FIG. 1.

The control box 102 includes a power source 106, e.g., electrical wall plug, for powering the device. The control box 102 also includes a control pad 108 and a display 110. The control pad 108 is used to set the temperature at which the vaporizer emits heated air. Referring briefly to FIG. 2, the display 110 is shown as reading a temperature of 343°. This temperature reading generally indicates the temperature at which air is being expelled from the control box 102.

Figure 3:
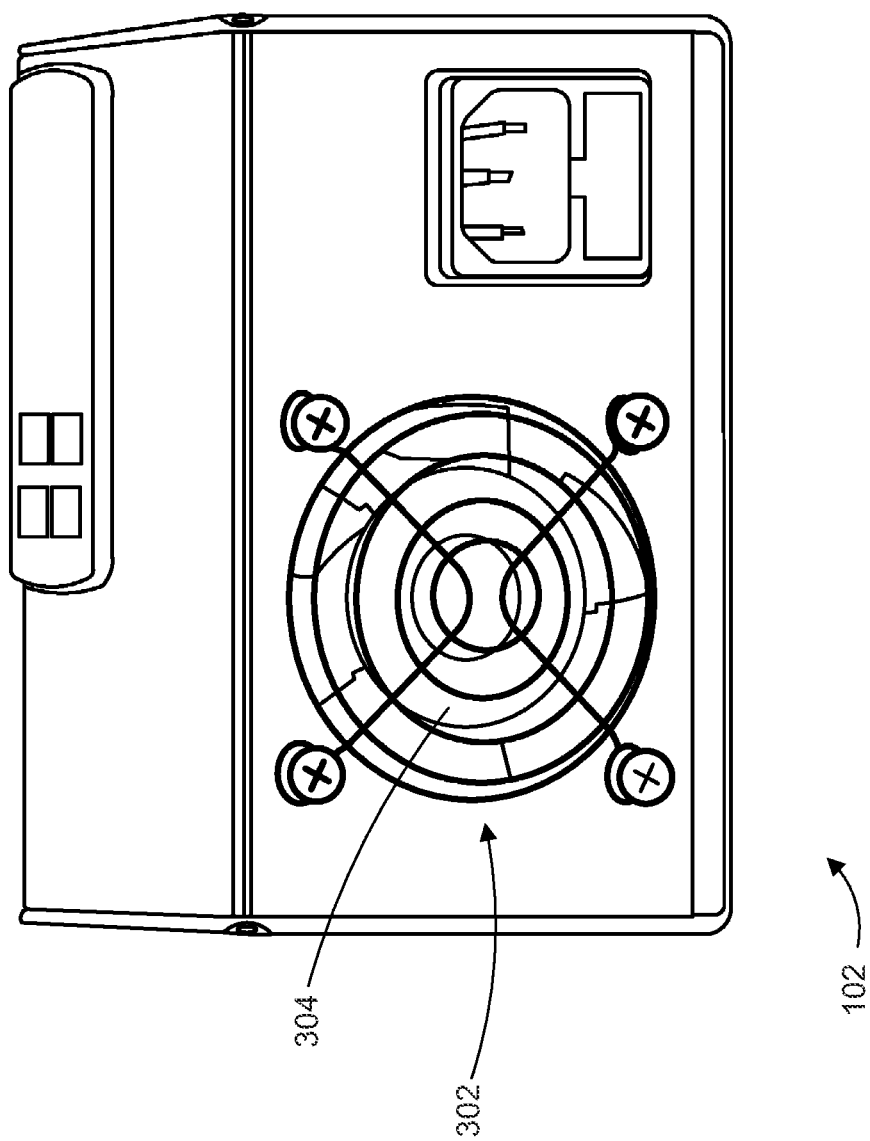
FIG. 3 is a close-up perspective rear view of the control box of FIG. 1.

FIG. 3 provides a perspective rear view of the control box 102 where an air intake hole 302 exposes a fan 304 housed within the control box 102. In operation, the fan 304 will pull air through the air intake hole 302 and cause it to pass through the control box 102 and into and through the whip 104.

Figure 4:
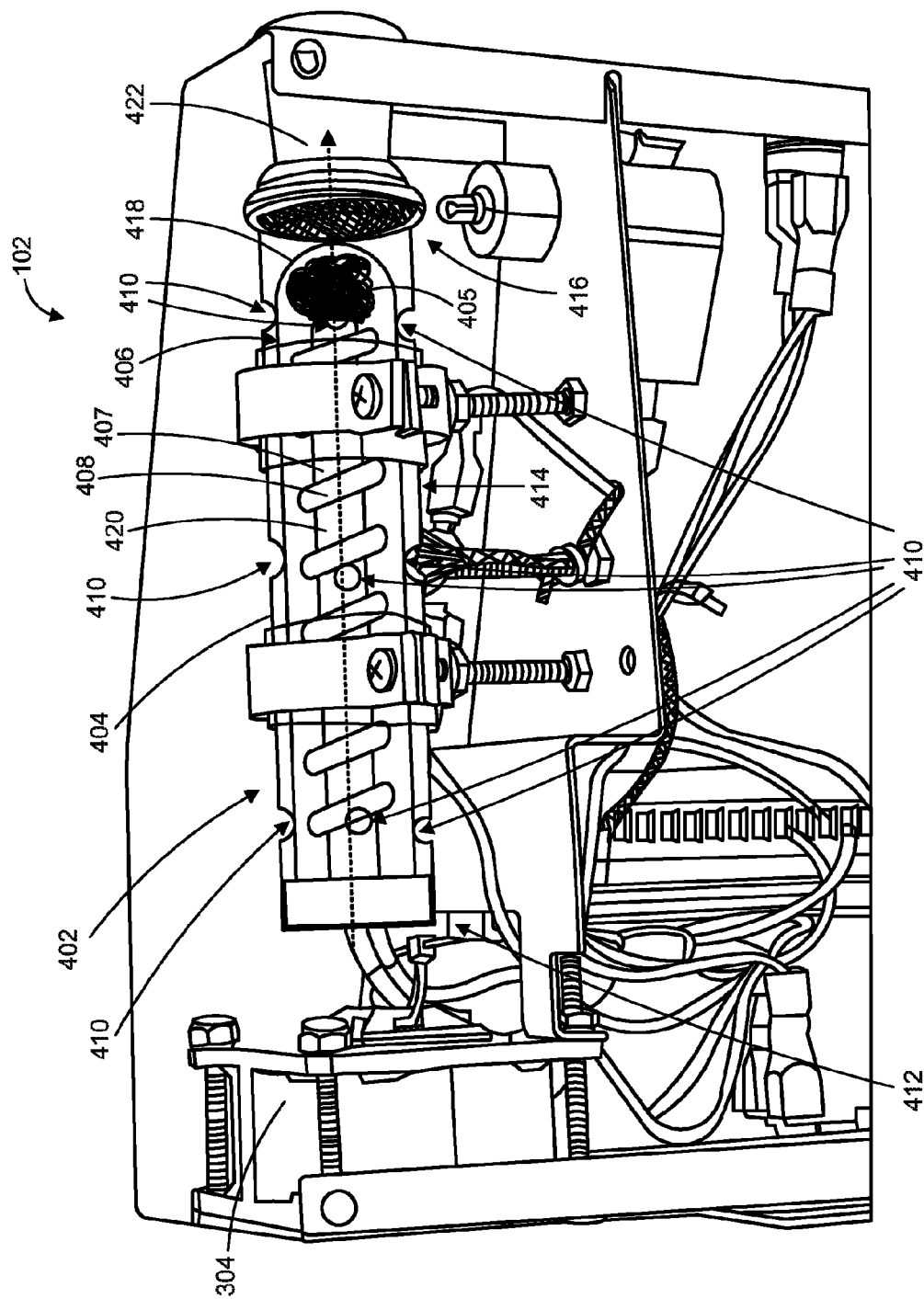
FIG. 4 is perspective partial view of the control box of FIG. 1 with the bottom cover removed, thereby exposing a heating and temperature-control assembly in accordance with an exemplary embodiment of the present invention.

FIG. 4 provides a perspective bottom view of the control box 102 with the bottom cover removed to expose components housed within the control box 102. One of the components clearly shown in this view is the heating assembly 402. The heating assembly 402 includes an elongated tubular airflow chamber 404. The elongated tubular airflow chamber 404 includes a proximal end 412, a distal end 416 opposite the proximal end 412, and a body 414 connecting the proximal end 412 to the distal end 416. In this embodiment, the elongated tubular outer airflow chamber 404 is made of glass which, conveniently, allows components within the elongated tubular airflow chamber 404 to be seen.

The elongated tubular airflow chamber 404 has a longitudinal central axis that passes through a center of the chamber 404, i.e., substantially equidistant from all portions of an interior wall of the chamber, and is parallel to the direction of airflow emitted from the fan 304. This longitudinal central axis is represented by the dashed line 405 shown in the view of FIG. 4.

The physical relationship between the elongated tubular airflow chamber 404 places the fan 304 in fluid communication with the proximal end 412 of the elongated tubular airflow chamber 404. When in operation, the fan 304 blows air into the proximal end 412 of the elongated tubular airflow chamber 404, through the glass body section 414 of the elongated tubular chamber 404, and out of the distal end 416 of the elongated tubular airflow channel 404. The arrowhead on the dashed line 405 indicates the direction of airflow from the fan 304.

Residing within the elongated tubular outer airflow chamber 404 is an elongated heating chamber 406, which can be seen in FIG. 4 because the elongated tubular outer airflow chamber 404 is transparent glass. In accordance with one embodiment of the present invention, a longitudinal central axis of the elongated heating chamber 406 is substantially collinear with the longitudinal central axis 405 of the airflow chamber 404.

In accordance with an exemplary embodiment of the present invention, both the elongated tubular outer airflow chamber 404 and the elongated heating chamber 406 are made of glass. The glass however does not have to be transparent.

The heating chamber 406 is disposed within the airflow chamber 404 and includes an elongated glass body 418 and a heating element 420 disposed within the elongated glass body 418 of the heating chamber 406. The elongated heating element 420 includes an elongated glass rod 407 and a heating coil 408 disposed on and supported by the elongated glass rod 407. As can be seen in FIG. 4, the conductive heating coil 408 is spiral wound around and along the length of the glass rod 407 of the heating element 420. The glass rod 407 can have a spiral groove that spans its length, allowing the heating coil 408 to seat within the spiral groove and remain stationary upon the glass rod 407. The elongated glass body 418 of the heating element 420 is sealed at both ends and prevents air from contacting the metallic heating coil 408.

An attachment adapter 422 is mechanically coupled to the distal end of the airflow chamber 404 in a sealing arrangement, i.e., so that air is funneled from within the airflow chamber 404 through the adapter 422. The attachment adapter 422 forms an attachment port for a vapor receiving element, such as the whip 104 shown in FIG. 1.

As can also be seen in FIG. 4, elongated tubular outer airflow chamber 404 has formed therein a plurality of concaved indentions 410 that point toward the interior of the elongated tubular outer chamber 404. The concaved indentions 410 are spaced to create a formation of nipple-like features on the interior of the elongated tubular outer chamber 404. The elongated heating chamber 406 rests on the apex of each of the inwardly-facing concaved indentions 410 so that the concaved indentions 410 support the elongated heating chamber 406 in a substantially center of the elongated tubular outer chamber 404.

The central location of the heating chamber 406 provides a substantially even spacing between an exterior surface of the heating chamber 406 and the interior surface of the elongated tubular airflow chamber 404. This uniform spacing advantageously allows air to flow around all sides of the heating chamber 406, thereby providing an efficient heat transfer between the entire surface of the heating chamber 406 and the air flowing through the interior of the elongated tubular airflow chamber 404.

In addition, because both the elongated tubular airflow chamber 404 and the elongated heating chamber 406 are made of glass, both are able to provide a long life of high-temperature operation without producing any additives or contaminants to the stream of air flowing past them, a problem plaguing the prior art, which uses materials such as ceramic.

Figure 5:
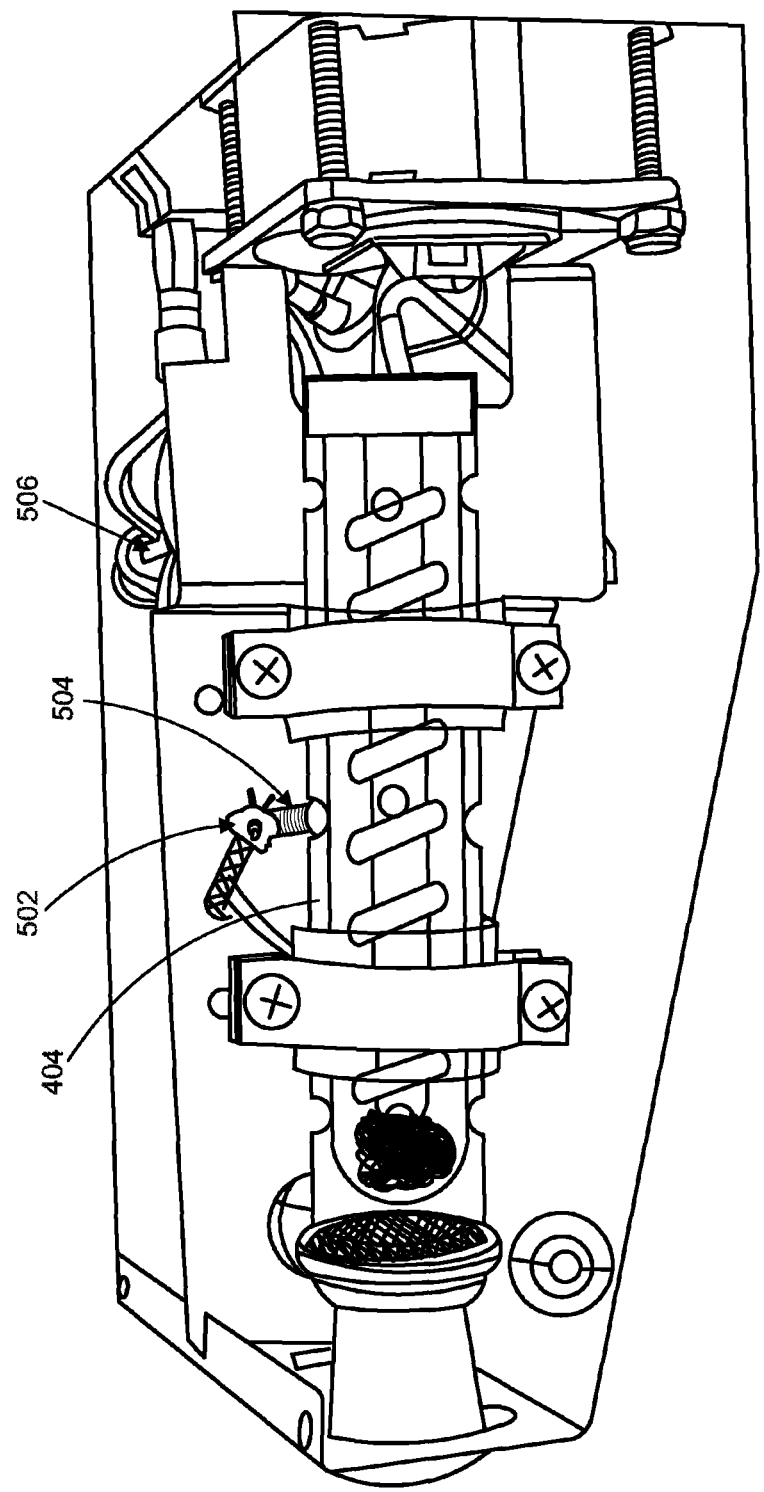
FIGS. 5-8 provide perspective views of the heating and temperature-control assembly of FIG. 4.
Figure 6:
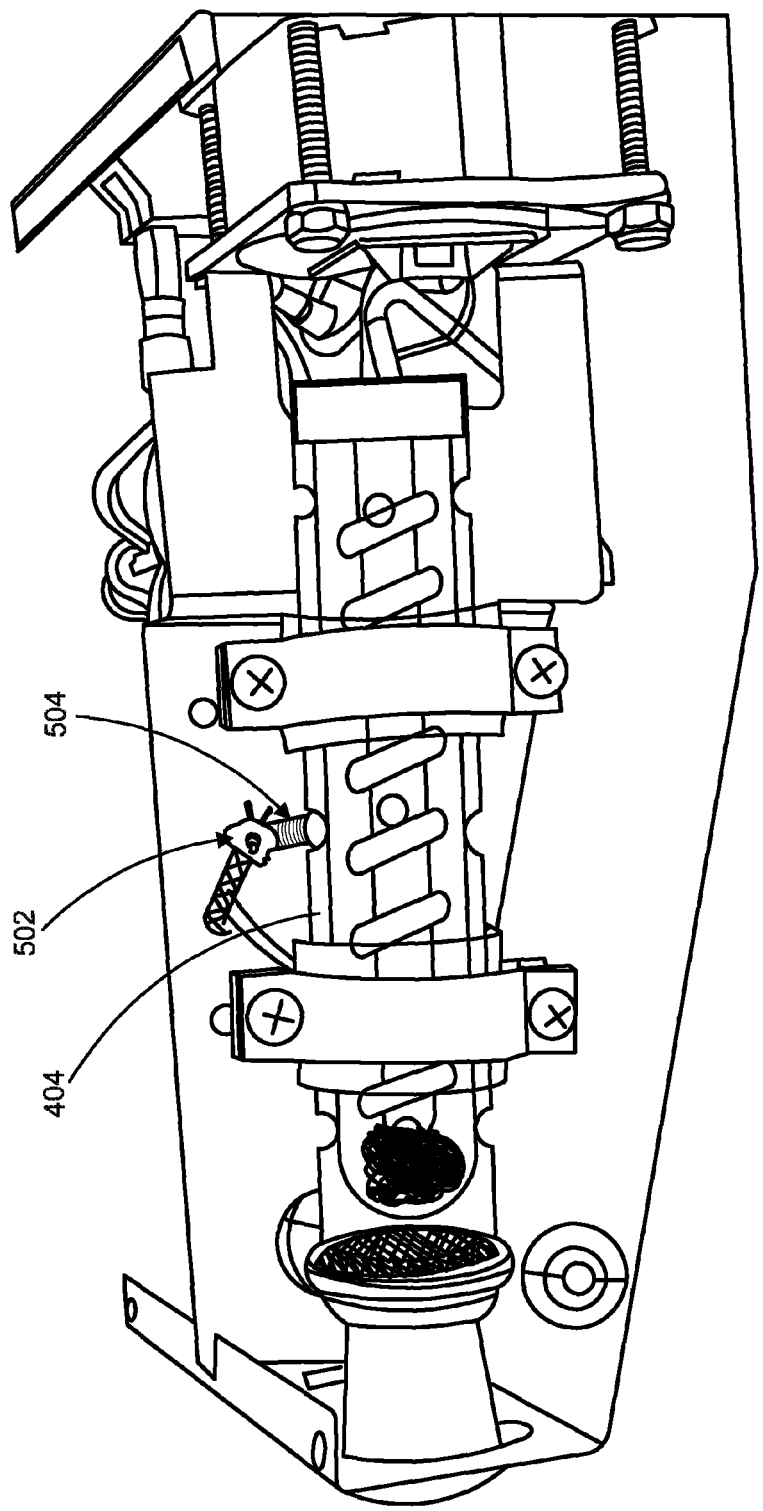
Figure 7:
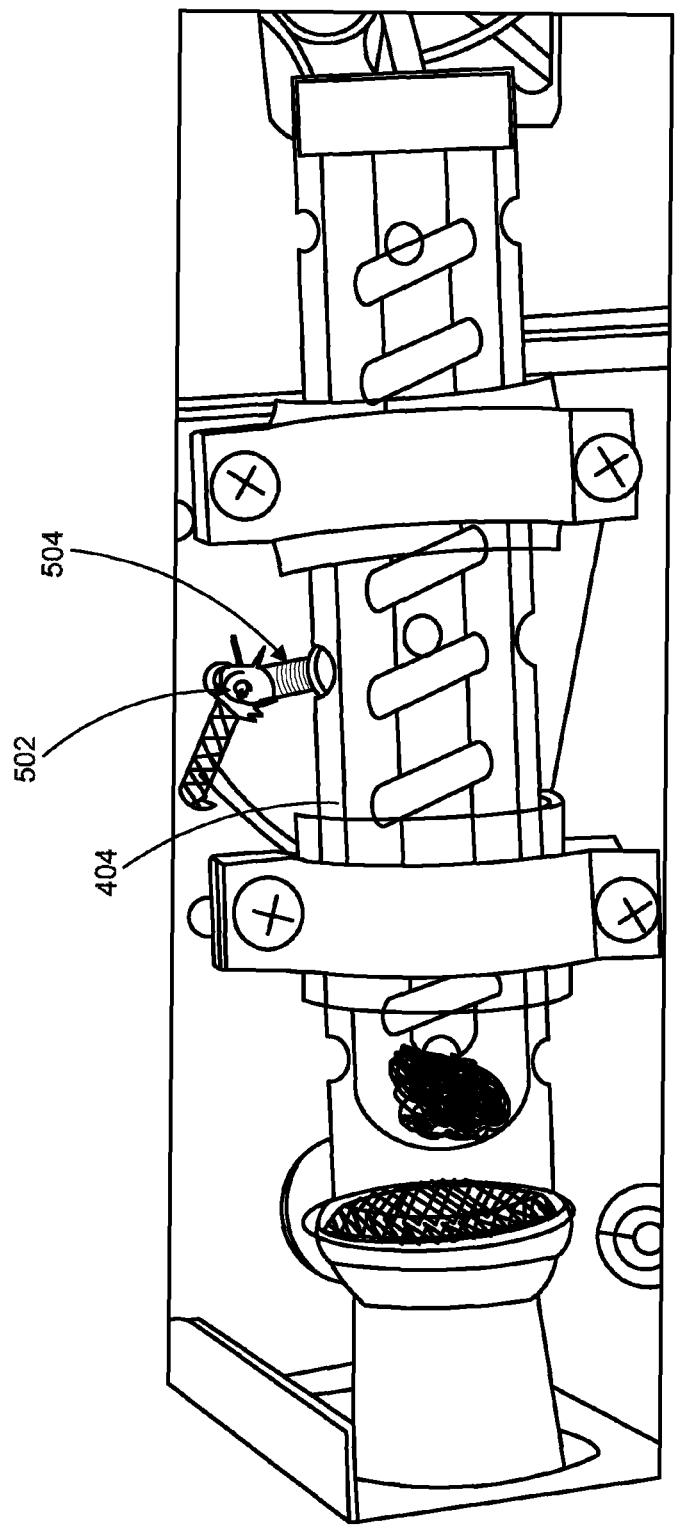
Figure 8:
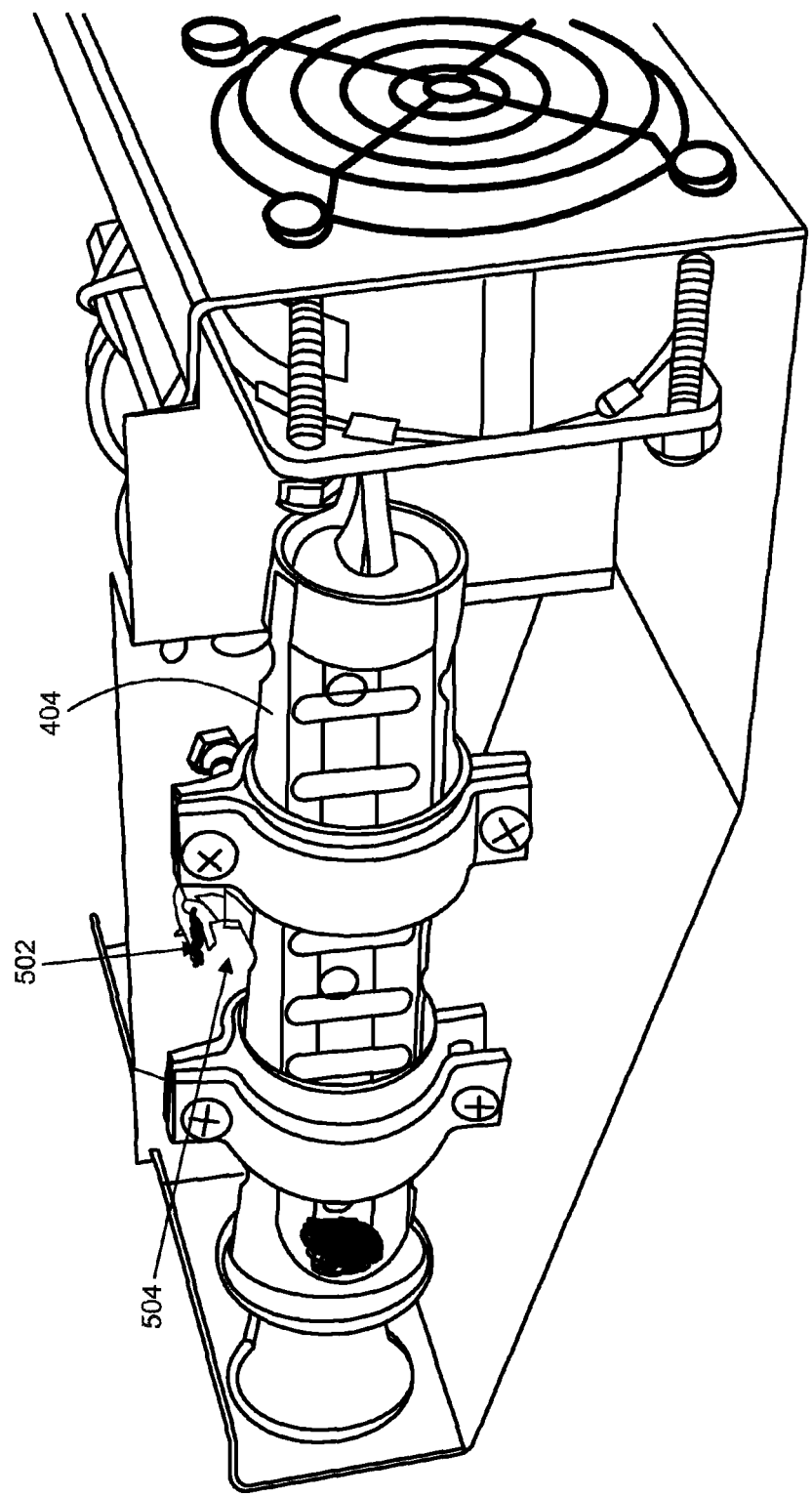

Referring now to FIGS. 5-9, an improved temperature sensing and control feature of the present invention is shown. Referring first to FIG. 5, a temperature probe 502 is positioned adjacent the elongated tubular airflow chamber 404 so that a space 504 exists between the temperature probe 502 and the elongated tubular airflow chamber 404. In other words, there is no physical connection between the temperature probe 502 and the elongated tubular airflow chamber 404. The space 504 can be as small as about 0.1 inches.

The temperature probe 502 is mechanically coupled to a temperature controller 506, which senses a temperature of the temperature probe 502 and controls current flowing through the heating coils 408 of the heating chamber 406 in response to the sensed temperature of the temperature probe 502. As opposed to prior-art vaporizer devices, where the temperature probe is installed within the interior of the heating assembly 402, the present invention provides a buffer. That is, where the prior-art probes are within the interior of the heating assembly 402, detect immediate changes in temperature within the interior of the heating assembly 402, and immediately send a signal in reaction to this temperature change, resulting in unnecessary fluctuations both up and down, the present invention provides a more stable control. More specifically, when one draws air from the whip 104 or other attachment, the temperature within the heating assembly 402 immediately drops in proportion to the amount of air being removed from within the airflow chamber 404. As the air removed from the whip 104 or other attachment, e.g., a bag attachment, is only a relatively small amount, the temperature drop within the airflow chamber 404 should only be temporary and does not need to be reacted to in a dramatic fashion. Advantageously, when the presently-inventive vaporizer is energized, the temperature probe 502 continuously measures air temperature around a portion, e.g., the center, of the exterior of the elongated tubular airflow chamber 404. The gap 504 between the tubular airflow chamber 404 and temperature probe 502 buffers the thermal coupling between the temperature probe 502 and the heating assembly 402 so that immediate drops in temperature within the airflow chamber 404 are not immediately responded to, Software, hardware, or a combination thereof 506, is programmed or preconfigured and calibrated to adjust and keep the heating element within the preselected temperature range, thus minimizing temperature fluctuation and uneven and/or contaminated vapor flow plaguing prior-art vaporizer's.

In accordance with a further embodiment, the present invention provides a dual-mode vapor delivery system, which provides the user with a choice between using the direct whip/wand style vapor inhalation instrument 104 or a balloon-type vapor inhalation instrument, both of which are well known in the art. Both instruments enjoy the benefits of the novel glass-on-glass airway defined by an interior surface of the airflow chamber 404 and an exterior surface of the heating chamber 406, thus creating the purest and most healthful vapor result available, cleanly through a completely sealed non contaminated glass air passage.

This novel device is able to utilize a touch screen control system that provides user-friendly prompts that allow the user, with one touch of a finger, to automatically control many operational features of the present invention. For example, the control system can select between at least two different temperature and fan speed functions. A higher fan speed is advantageous for a bag-type inhalation instrument and provides a user friendly experience, regardless of the user's delivery system preference.

The balloon vapor filling system is enabled by utilization of a variable speed fan, which forces air from a rear of the unit through and "airseal" funnel, which is attached in a sealed fashion to the glass airflow chamber 404. The airseal funnel advantageously fluidly connects the fan and the glass air chamber 404, which contains the sealed glass heating chamber 406.

A vaporizer heating device has been disclosed that provides a novel glass-on-glass airway defined by an interior surface of the airflow chamber 404 and an exterior surface of the heating chamber 406, thus creating the most pure and healthy vapor possible delivered through a completely sealed, non-contaminated glass air passage.

What is claimed is:

1. A vaporizer heating assembly comprising:
   a vapor inhalation device shaped to contain a vapor and deliver the vapor to a user's mouth without expelling the vapor into the atmosphere;
   an airflow chamber mechanically coupled to the vapor inhalation device;
   a heating chamber disposed within the airflow chamber;
   a fan in fluid communication with an air passageway defined by an interior surface of the airflow chamber and an exterior surface of the heating chamber;
   a temperature probe disposed proximate and external to the airflow chamber, but not in direct physical contact with the airflow chamber, the temperature probe adapted to measure an air temperature surrounding a portion of the exterior of the airflow chamber;
   a distance between the airflow chamber and the temperature probe, the distance adapted to buffer a thermal coupling between the temperature probe and the heating chamber; and
   a temperature controller thermally coupled to the temperature probe and communicatively coupled to the heating chamber, the temperature controller operable to control a temperature output of the heating chamber in response to temperature information received from the temperature probe.

2. The vaporizer heating assembly according to claim 1, wherein:
   the distance between the temperature probe and the airflow chamber is at least about 0.1 inches.

3. The vaporizer heating assembly according to claim 1, wherein the airflow chamber comprises:
   a proximal end;
   a distal end coupled to the vapor inhalation device; and
   a glass body connecting the proximal end to the distal end.

4. The vaporizer assembly according to claim 1, wherein the glass heating chamber comprises:
   an elongated glass body; and
   a heating element disposed within the elongated glass body of the heating chamber.

5. The vaporizer assembly according to claim 4, wherein the heating element comprises:
   an elongated glass rod; and
   a heating coil disposed on and supported by the elongated glass rod.

6. The heating assembly according to claim 1, wherein:
   the airflow chamber defines a longitudinal central axis; and
   a longitudinal central axis of the heating chamber is substantially collinear with the longitudinal central axis of the airflow chamber.

7. The heating assembly according to claim 1, wherein:
   a location of the heating chamber within the airflow chamber provides an airflow path between the heating chamber and an interior surface of the airflow chamber on all sides of the heating chamber.

8. A vaporizer assembly comprising:
   a heating assembly including:
      a tubular airflow chamber having:
         a proximal end;
         a distal end opposite the proximal end; and
         a glass body connecting the proximal end to the distal end, the glass body having a plurality of indentions extending into an interior defined by the glass body; and
      a heating chamber disposed within the airflow chamber, the heating chamber having:
         an elongated glass body; and
         a heating element disposed within the elongated glass body of the heating chamber;
   a fan in fluid communication with an air passageway defined by an interior surface of the airflow chamber and an exterior surface of the heating chamber and operable to cause air to flow into the proximal end of the airflow chamber, across all sides of the heating element, and out of the distal end of the airflow chamber;
   a vapor inhalation device mechanically coupled to the distal end of the airflow chamber and shaped to contain a vapor received from the airflow chamber and deliver the vapor to a user's mouth without expelling the vapor into the atmosphere;
   a temperature probe disposed proximate, but not in direct physical contact with the airflow chamber; and a temperature controller thermally coupled to the temperature probe and communicatively coupled to the heating chamber, the temperature controller operable to control a temperature output of the heating chamber in response to temperature information received from the temperature probe.

9. The vaporizer assembly according to claim 8, further comprising:
an attachment adapter mechanically coupled to the distal end of the airflow chamber in a sealing arrangement, the attachment adapter forming an attachment port for the vapor inhalation device.

10. The vaporizer assembly according to claim 8, wherein the airflow chamber further comprises:
a plurality of interiorly-pointing features along an interior wall of a glass body of the airflow chamber,
wherein the heating chamber is physically supported by the plurality of interiorly-pointing features.

11. The vaporizer assembly according to claim 8, wherein the elongated glass body comprises:
a spiral groove defined by an outer surface of the elongated glass body and spanning a length of the elongated glass body, wherein the heating coil is seated within the spiral groove.

12. The vaporizer assembly according to claim 8, further comprising:
a filter at the distal end of the airflow chamber.

13. A method of regulating a temperature within a vaporizer heating assembly, the method comprising:
providing a vaporizer heating assembly that includes:
a vapor inhalation device shaped to contain a vapor and deliver the vapor to a user's mouth without expelling the vapor into the atmosphere;
an airflow chamber mechanically coupled to the vapor inhalation device;
a heating chamber disposed within the airflow chamber;
a fan in fluid communication with an air passageway defined by an interior surface of the airflow chamber and an exterior surface of the heating chamber;
a temperature probe disposed proximate and external to the airflow chamber, but not in direct physical contact with the airflow chamber, the temperature probe adapted to measure an air temperature surrounding a portion of the exterior of the airflow chamber;
a distance between the airflow chamber and the temperature probe, the distance adapted to buffer a thermal coupling between the temperature probe and the heating chamber; and
a temperature controller thermally coupled to the temperature probe and communicatively coupled to the heating chamber, the temperature controller operable to control a temperature output of the heating chamber in response to temperature information received from the temperature probe;
sensing a temperature of an area surrounding a portion of the airflow chamber with the temperature probe;
communicating the sensed temperature of the area surrounding a portion of the airflow chamber to the temperature controller;
operating the fan to direct air into a proximal end of the airflow chamber;
sensing with the temperature probe a change in the temperature of the area surrounding the portion of the airflow chamber; and
communicating the sensed temperature change to the temperature controller.

14. The method according to claim 13, wherein:
the distance between the temperature probe and the airflow chamber is at least about 0.1 inches.

15. The method according to claim 13, wherein the airflow chamber comprises:
a proximal end;
a distal end coupled to the vapor inhalation device; and
a glass body connecting the proximal end to the distal end.

16. The method according to claim 13, wherein the glass heating chamber comprises:
an elongated glass body; and
a heating element disposed within the elongated glass body of the heating chamber.

17. The method according to claim 16, wherein the heating element comprises:
an elongated glass rod; and
a heating coil disposed on and supported by the elongated glass rod.

18. The method according to claim 13, wherein:
the airflow chamber defines a longitudinal central axis; and
the heating chamber is supported substantially along the longitudinal central axis.

19. The method according to claim 13, wherein:
a location of the heating chamber within the airflow chamber provides an airflow path between the heating chamber and an interior surface of the airflow chamber on all sides of the heating chamber.

* * * * *